United States Patent [19]

Spiegel

[11] Patent Number: 4,870,161

[45] Date of Patent: Sep. 26, 1989

[54] REAGENTS AND PROBES FOR DISTINGUISHING AND ISOLATING DIFFERENT GTP-BINDING PROTEINS

[75] Inventor: Allen M. Spiegel, Bethesda, Md.

[73] Assignee: The United States of America as represented by the Department of Health and Human Services, Washington, D.C.

[21] Appl. No.: 100,909

[22] Filed: Sep. 25, 1987

[51] Int. Cl.⁴ .............................................. C07K 7/08
[52] U.S. Cl. .................................... 530/326; 530/325
[58] Field of Search .............................. 530/326, 328

[56] References Cited

PUBLICATIONS

Goldsmith et al., *J. Biol. Chem.*, 1-6, (1987).

Primary Examiner—Delbert R. Phillips
Attorney, Agent, or Firm—Fleit, Jacobson, Cohn, Price, Holman & Stern

[57] ABSTRACT

Substantially pure, synthetic peptides corresponding to specific epitopic sites of various G-proteins and antibodies having binding affinity specifically for said epitopic sites have been prepared. Kit and method for identifying various G-proteins are also disclosed.

6 Claims, 4 Drawing Sheets 1  2  3  4  5  6  7  8

$-a_i$ 1 2 3 4 5 6 7 8

$-a_i$

Coomassie Blue 1  2  3

$-a$
$-\beta$

LE/3

1  2  3

CW/6

1  2  3

AS/6

1  2  3

$-a$
$-\beta$

REAGENTS AND PROBES FOR DISTINGUISHING AND ISOLATING DIFFERENT GTP-BINDING PROTEINS

BACKGROUND OF THE INVENTION

The present invention is related to guanine nucleotide-binding proteins. More particularly, the present invention is related to specific reagents and probes for identifying, isolating and distinguishing between different guanine nucleotide (GTP)-binding proteins.

State of The Art:

GTP-binding (hereinafter "G" proteins) comprise a family of distinct but related signal transducers. One or more members of the family is found in virtually every type of cell, and performs a critical role in the transduction of hormonal, neurotransmitter, cytokine, odorant, and light signal functions. G-proteins are known to be heteromeric; the alpha-GTP-binding subunit is distinct for each member of the G-protein family and is believed to confer specificity in both receptor and effector interactions.

A combination of protein purification and recombinant DNA techniques have led to the realization that the G-protein family consists of at least 7 distinct members. Cloning of complementary DNA for each of these allows prediction of the amino acid sequence. The proteins include 2 forms of "transducin" (TD), a G-protein uniquely found in retinal photoreceptors and involved in phototransduction, and five other proteins termed $G_s$, $G_o$, $G_{i1}$, $G_{i2}$, and $G_{i3}$. The specific functions of each of these is as yet unclear, but they appear to regulate ion channels and enzymes that generate intercellular "second messengers." Although each protein shows significant amino acid sequence homology (ranging from 40% for $G_s$ vs. $G_i$, to 90% for $G_{i1}$ vs. $G_{i3}$), there are unique sequence differences in each.

Certain bacterial toxins, particularly pertussis toxin, covalently modify certain G-proteins and this technique has been used for identification of G-proteins. However, this method is relatively nonspecific as transducin (TD), $G_o$, and all forms of $G_i$ appear to be pertussis toxin substrates. For this reason, several laboratories have generated antibodies against G-proteins to obtain more specific probes. The majority of these reagents, whether polyclonal rabbit antisera or monoclonal mouse antibodies are of undefined epitope, and are not particularly specific for a single G-protein so as to definitively distinguish one from the other. Moreover, none of the known antibodies can be used to block specific functional interactions of G-proteins.

SUMMARY OF THE INVENTION

It, is, therefore, an object of the present invention to provide synthetic peptides corresponding to specifically defined sequences of G-protein alpha subunits.

It is another object of the present invention to provide antisera or purified antibodies having binding affinity exclusively for a particular epitopic site of a G-protein.

It is a further object of the present invention to provide a reagent kit for identifying or distinguishing between specific G-proteins.

It is yet another object of the present invention to provide unique probes for isolating specific G-protein antibodies in substantially pure form.

Other object and advantages of the present invention will become evident from the Detailed Description of the Invention.

BRIEF DESCRIPTION OF THE INVENTION

These and other objects, features and many of the attendant advantages of the invention will be better understood upon a reading of the following detailed description when considered in connection with the accompanying drawings wherein:

FIG. 1 shows the detection of Gi-alpha mono-ADP-ribosylated by pertussis toxin with AS/7. C6 glioma cells were treated in culture for 16 hours with: a) no toxin, b) 100 ng/ml pertussis toxin, c) 100 ng/ml cholera toxin. A crude plasma membrane fraction was then prepared and 50 µg/lane membrane protein were separated by SDS-PAGE on a 10% gel. Immunoblots were performed as described in the specification, except that a 1:500 dilution of second antibody was used, and O-diansidine (0.025% solution) was used as substrate for the enzyme-2nd antibody conjugate. A 1:100 dilution of AS/7 was used as first antibody. The positions of molecular weight standards are indicated;

FIG. 2 shows the detection of brain "Gi-alpha" with AS/6 and 7. 100 µg/lane of cholate extract of bovine cerebral cortical membranes were separated by SDS-PAGE on a 10% gel and immunoblotted, except that samples were treated with N-ethylmaleimide before SDS-PAGE. Antisera used were: affinity purified RV/3 (panels A and B) at lanes 1 and 2—1:20 dilution, and lane 3—1:40 dilution; AS6 (panel A) and AS7 (panel B) at lane 2—1:40, lane 3—1:200 dilution, and lane 4—1:100 dilution. The positions of alpha subunits of Gi and Go and of the common beta subunit are indicated;

FIG. 3 shows the detection of "Gi-alpha" in brain and neutrophil with antisera LE/1,2 and 3 and AS/6 and 7. In panel, A, 50 µg/lane of highly purified human neutrophil plasma membranes, and in panel B, 150 µg of bovine brain membrane cholate extract were separated by SDS-PAGE on a 10% gel and immunoblotting performed. Antisera used were: preimmune LE/1 (lane 1), immune LE/1 (lane 2), preimmune LE/2 (lane 3), immune LE/2 (lane 4), preimmune LE/3 (lane 5), immune LE/3 (lane 6), immune AS/6 (lane 7), and immune AS/7 (lane 8). LE/1, 2 and 3 (immune and preimmune) were used at 1:100 dilution, and AS/6 and 7 were used at 1:250 dilution. The position of the Gi-alpha subunit is indicated; and FIG. 4 shows the reactivity of antisera with purified GTP-binding proteins. The major pertussis toxin substrate (alpha subunit only) purified from bovine neutrophils (lane 1), Gi/Go purified from bovine brain (lane 2), and holotransducin (lane 3) purified from bovine rod outer segments were separated by SDS-PAGE on a 10% gel. In panel A, the gel was stained for protein, and in panel B immunoblotting was performed with the indicated antisera (LE/3 and CW/6, 1:100 dilution; AS/6, 1:250 dilution). In lane 1 panel A 0.5 µg was loaded, in the lane 1 panel B 1.0 µg was loaded. In lane 2 (A and B), 4 µg were loaded, and in lane 3 (A and B) 2 µg were loaded. The positions of alpha and beta subunits are indicated.

DETAILED DESCRIPTION OF THE INVENTION

Figure 1:
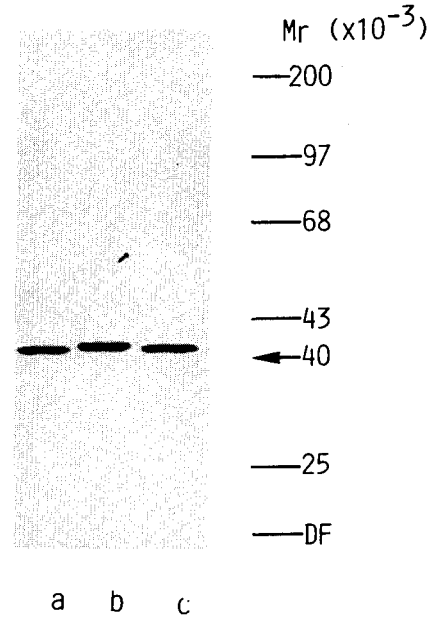

The above and various other objects and advantages of the present invention are achieved by providing antisera or isolated, substantially pure antibodies having binding affinity for specific synthetic epitope of G-protein.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "substantially" pure as used herein means that the preparation is as pure as can be obtained employing standard techniques well known to one of ordinary skill in the art.

MATERIALS AND METHODS Peptide synthesis: The synthetic peptides were assembled stepwise by the Merrifield solid-phase method (Barany et al, *The Peptides* 2A:1–284, 1979), using an Applied Biosystems 430A automated peptide synthesizer. The peptide resins were cleaved with anhydrous hydrogen fluoride and the crude peptides were purified by preparative liquid chromatography on reverse-phase C18. The purified peptides were homogeneous by analytical high-performance liquid chromatography, and gave amino acid compositions consistent with those theoretically expected. Table 1 lists the amino acid sequences of the synthetic peptides and the designation of the rabbit antisera produced therefrom.

TABLE 1

| Amino Acid Sequence Of Synthetic Peptides (Single Letter Code) | Designation Of The Antisera vs Synthetic Peptide |
|---|---|
| KENLKDCGLF | AS/6, AS/7 |
| LERIAQSDYI | LE/2, L3/3 |
| LDRIAQPNYI | LD/1, LD/2 |
| ANNLRGCGLY | GO/1, GO/3 |
| GCTLSAEERAALERSK | GC/1, GC/2 |

Peptide Conjugation and Immunization: 10 mg of keyhole limpet hemocyanin (KLH, Sigma) and 3 mg of peptide were dissolved in 1.0 ml of 0.1M phosphate buffer, pH 7.0, 0.5 ml of 21 mM glutaraldehyde (also in 0.1M phosphate buffer, pH 7.0) was then added dropwise with stirring and the combined 1.5 ml were incubated for about 24 hours at room temperature (about 22° C.–25° C.). The 1.5 ml solution was mixed with an equal volume of complete Freund's adjuvant and 1 ml aliquots of the resulting emulsion were injected in multiple intradermal sites in 3 New Zealand white rabbits. Four weeks later each animal received a booster immunization with material prepared identically except that ½ as much peptide and KLH were injected in incomplete Freund's adjuvant. Preimmune sera were collected, and subsequent bleeds were performed weekly, beginning two weeks after booster immunization. Affinity-purification of antibodies from the antisera was accomplished by standard techniques using immobilized holoTD as described for example by Gierschik et al, 1986 (*Proc. Natl. Acad. Sci USA* 83:2258–2262). The purified antibodies are conveniently cryopreserved in suitable buffers.

Membrane Preparations: Human neutrophils were isolated and plasma membrane-enriched fractions prepared as described by Falloon et al, (*FEBS Letters* 209:3520356, 1986). C6 glioma cells were cultured and membrane preparations made as described by Milligan et al, (*FEBS Letters* 195:225–230, 1986). Bovine brain membrane fractions and cholate extracts were made as described by Sternweis et al (*J. Biol. Chem.* 259,13806–13813, 1984) and Gierschik et al (supra).

Protein Purification: Synthetic peptides of the present invention were employed as probes for affinity purification of specific antibodies following standard methodology well known in the art. TD was purified from bovine rod outer segment membranes as described by Gierschik et al. (*Proc. Natl. Acad. Sci. USA* 82:727–731, 1985). A mixture of Gi and Go was purified from bovine brain as described by Milligan et al, (*J. Biol. Chem.* 260:2057–2063, 1985) and Gierschik et al, 1986 (supra.). The "48 k" protein was purified from bovine retinas as described by Zigler et al, (*Invest Ophthalmol. Vis. Sci.* 25:977–980. 1984). The major pertussis toxin substrate of bovine neutrophils was purified as the isolated alpha subunit.

Other methods: SDS-PAGE and immunoblotting were performed as described by Gierschik et al, (supra. 1985) and Giersohik et al, (*J. Biol. Chem.* 261:8058–8062, 1986). Incubation with first antibody solutions were for about 24 hours at room temperature. Dilutions of antisera used in first antibody solutions have been indicated, supra. Second antibody, peroxidase-conjugated goat anti-rabbit Ig (Kierkegarrd and Perry), was used at a 1:300 dilution, and incubation was for about 2 hours at room temperature. 4-chloronaphthol (Sigma) was used as substrate for peroxidase. Pertussis toxin (List Biochemicals) was activated and used in ADP-ribosylation reactions with either nonradioactive NAD (1 mM) or 32P-alpha-NAD (10 μM) as described by Eide et al, (*Biochemistry* 25:6711–6715, 1986).

FIGS. 1–4 present data showing specificity of various antisera or antibody reagents of the present invention with respect to various G-proteins. A summary of the results obtained is presented in Table 2. It should be noted that the cascade of the antibody reagent of the present invention for the first time enables identification and differentiation between various members of the G-protein family including subtyping of new ones. In addition, the availability of the isolated, purified antibodies allow the determination of the functional role of specific G-proteins by interacting receptor or effector sites with the antibodies or a fragment or conjugate thereof. Technique used for such studies are well known to one of ordinary skill in the art to which this invention belongs.

TABLE 2

Specificity of Various Rabbit Antisera to Particular G-Proteins

| Antisera | | Specificity |
|---|---|---|
| AS/6 | AS/7 | Specific for TD (both forms) and for $G_{i1,2,3}$ but not for $G_o$. Blocks receptor-G-protein coupling. |
| LE/2 | LE/3 | Specific for $G_{i2}$ only. |
| LD/1 | LD/2 | Specific for $G_{i1}$, and not $G_o$ or $G_{i2}$. |
| GO/1 | GO/3 | Specific for $G_o$ only. Blocks receptor-G-protein coupling. |
| GC/1 | GC/2 | Reacts primarily with $G_o$; to lesser extent with $G_i$ forms. |

In contrast, the antisera or antibody reagents heretofore known either completely lack or have limited specificity for particular G-proteins so as to allow distinction between them. Table 3 comparatively lists the properties of prior art antibodies. It should be noted that the prior art antibodies were in general prepared by employing the entire (holo) protein and not by using specific epitopes, identified and synthesized as in the present invention. Hence, the prior art antibody reagents lack specificity, i.e. for such G-proteins as $G_{i1,2,3}$ OR $G_o$ and the like. Thus, differentiation between the various subtypes of the G-protein family is simply not possible with heretofore available antibody reagents.

TABLE 3

| Reference | Type Ab | Specificity | Antigen Used |
|---|---|---|---|
| Gierschik et al PNAS 82:727, 1985 | polyclonal | TD | Raised vs. pure holo-protein |
| Gierschik et al PNAS 83:2258, 1986 | polyclonal | $G_o$ | Raised vs. pure holo-protein |
| Huff et al JBC 260:10864 1985 | polyclonal | $G_o$ | Raised vs. pure holo-protein |
| Tsai et al Biochem 26: 4728, 1987 | polyclonal also monoclonal | $G_o$ TD | Raised vs. pure holo-protein Raised vs. TD but crossreacted $G_i$. |
| Asano et al J. Neurochem 48:1617, 1987 | polyclonal | $G_o$ | Raised vs. pure holo-protein |
| Homburger et al Mol. Pharm 31:313 1987. | polyclonal | $G_o$ | Raised vs. pure holo-protein |
| Katada et al FEBS Letters 213:353, 1987 | polyclonal | $G_o$, $G_i$ | Raised vs. pure holo-protein. May have specificity vs. $G_i$ |
| Lerea et al Science 234: 77, 1986 | polyclonal | TD rod TD cone | Raised vs. synthetic peptides; specific only for TD but not for $G_{i1,2,3}$. |
| Mumby et al PNAS 83:265 1986 | polyclonal | TD | Raised vs. pure holo-protein. |
|  |  | $G_o$ | Raised vs, pure holo-protein. |
|  |  | $G_o$ | Raised vs. synthetic peptide but used an entirely different synthetic peptide than the peptide used in the present invention. |
|  |  | Reacts with all G-proteins and lacks specificity for any particular G-protein. | Raised vs. synthetic peptide entirely different from the peptides employed in the present invention. |

The decapeptide, KENLKDCGLF, corresponding to the carboxylterminus of both rod and cone transducin-alpha includes the cystein residue that is the site of pertussis toxin-catalyzed ADP-ribosylation. As mentioned above, the synthetic peptide was conjugated to LKH and three rabbits designated AS/6, 7, and 8 immunized with the peptide KLH conjugate. Preimmune and postimmunization bleeds from each animal were tested for specific reactivity on immunoblots of purified holotransducin. For comparison, an immune bleed of rabbit, AS/1 immunized with holotransducin was also tested. All three peptide immunized rabbits developed antibodies against transducin-alpha; preimmune sera showed no reactivity. By comparison, AS/1, as previously reported (Gierschik et al supra. 1985), recognizes all three transducin subunits, alpha, beta and gamma without distinguishing between them.

The carboxyl-terminal decapeptide of transducin-alpha shows some homology to the carboxylterminus of transducin-gamma as well as to an internal sequence of the "48k" protein of rod outer segments. The latter homology may reflect the involvement of this domain in receptor interaction. The reactivity of antisera AS/6 and AS/7 against these related sequences was tested by performing immunoblots with holotransducin and the purified 48k protein. AS/6 and AS/7 reacted exclusively with transducin-alpha; AS/1, a holotransducin antiserum, readily recognized transducin-gamma (as well as beta) in this test and both anti-48k sera tested reacted strongly with this protein (data not shown).

It was of interest to determine if antisera raised against the synthetic peptide, KENLKDCGLF, could recognize this sequence after ADP-ribosylation on cysteine by pertussis toxin.

To test this, two types of experiments were performed. In the first, intact C6 glioma cells were treated with pertussis toxin, cholera toxin, or no toxin and then the reactivity was tested on immunoblots of AS/7 with a membrane preparation from each set of cells. Treatment of intact C6 glioma cells with pertussis toxin abolished subsequent ADP-ribosylation of a 40-kDa protein in membranes from treated cells incubated with pertussis toxin and [alpha-$^{32}$P]NAD (not shown). Antisera raised against KENLKDCGLF, react with 40-41-kDa protein(s) in most cells tested (vide infra) including C6 glioma cells. FIG. 1 shows the reactivity of AS/7 with a 40-Da protein in C6 glioma cell membranes from cells incubated without toxin or with cholera toxin. In cell membranes from cells incubated with pertussis toxin, immunoreactivity is not reduced by the migration of the reactive protein and is slightly reduced as expected after ADP-ribosylation. In a second type of experiment, purified holotransducin was incubated with pertussis toxin for varying times under conditions leading to increasing degrees of ADP-ribosylation. PG/1, an antiserum raised against chemically conjugated ADP-ribose reacts with ADP-ribosylated, but not unmodified, transducin-alpha and showed an increase in ADP-ribosylation of the transducin-alpha subunit with increasing time of incubation with pertussis toxin, in agreement with the results of the experiment shown in FIG. 1. AS/7 reactivity with transducin-alpha is not affected by pertussis toxin-catalyzed ADP-ribosylation (data not shown).

Sequencing of cDNA clones encoding G-protein alpha subunits allows comparison of the amino acid sequence of the synthetic peptide, KENLKDCGLF, with that predicted by the cDNA clones. Table 4 shows such a comparison and indicates that both $G_{i\alpha-1}$ and $G_{i\alpha-2}$ differ from the synthetic peptide sequence by a single residue. In contrast, $G_{o\alpha}$ differs by 5–10 residues. $G_{s\alpha}$ (not shown) shares only 2 residues in common with the synthetic peptide. Based on this comparison it was reasoned that antisera raised against KENLKDCGLF might recognize $G_{i\alpha-1}$ and $G_{i\alpha-2}$ subunits, but not $G_{o\alpha}$.

TABLE 4

Comparison of amino acid sequence of synthetic peptide corresponding to transducin-alpha 341-350 to homologous sequences of other G-protein alpha subunits. Since the amino sequence of $G_o$ has not been published, residue numbers are not shown. (The single letter amino acid code is used.)

| $G_{i\alpha\text{-}1}$ (345–354): | K N N L K D C G L F |
|---|---|
| $G_{i\alpha\text{-}2}$ (346–355): | K N N L K D C G L F |
| Transducin rod (341–350): | K E N L K D C G L F |
| Transducin cone (345–354): | K E N L K D C G L F |

TABLE 4-continued

Comparison of amino acid sequence of synthetic peptide corresponding to transducin-alpha 341-350 to homologous sequences of other G-protein alpha subunits. Since the amino sequence of $G_o$ has not been published, residue numbers are not shown. (The single letter amino acid code is used.)

| $G_o$ | A N N L R G C G L Y |
|---|---|

Figure 2A:
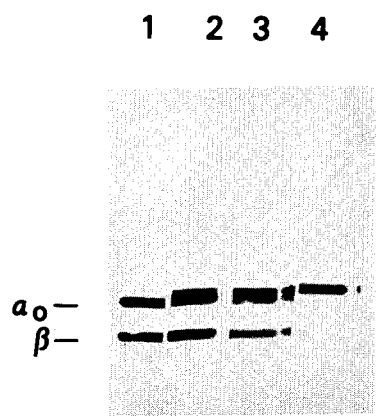
Figure 2B:
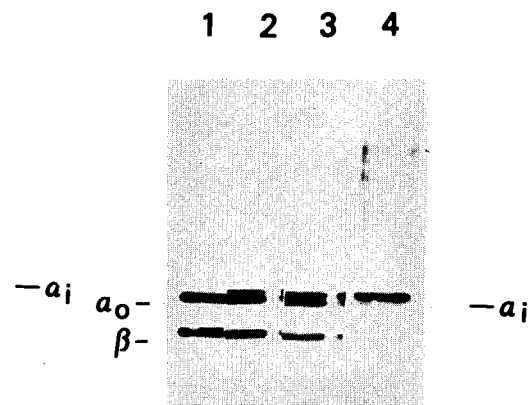

To test this hypothesis, immunoblots were performed as shown in FIG. 2. A crude brain membrane preparation or a cholate extract of such membranes contained both $G_i$ and $G_o$. Antisera AS/6 and AS/7 revealed an immunoreactive band at 40-41 kDa in cholate extracts of brain membranes (FIG. 2, lanes A4 and B4). In contrast, antiserum RV/3 raised against a mixture of purified brain $G_i$ and $G_o$ and previously shown to recognize $G_{o\alpha}$ and the common beta subunit reveals 39- and 36-kDa immunoreactive bands, as expected (lane 1). By mixing either AS/6 and RV/3 or AS/7 and RV/3, it was demonstrated (lanes 2 and 3) that AS/6 and AS/7 recognizes protein(s), presumably $G_{i\alpha}$ distinct from those recognized ($G_{o\alpha}$ and $G_{o\beta}$) by RV/3. Identical results were obtained with purified $G_i/G_o$ preparations (not shown).

Antisera raised against KENLKDCGLF thus react with transducin-alpha and $G_{i\alpha}$ but not $G_{o\alpha}$. These antisera, however, cannot discriminate between $G_{i\alpha-1}$ and $G_{I\alpha-2}$ which share the identical KNNLKDCGLF sequence (Table 4).

To develope a reagent capable of discriminating between these two closely related (88% homologous) sequences, a particular sequence was chosen to prepare antisera capable of differentiating rod and cone transducin-alpha subunits. The sequence of the decapeptide synthesized, LERIAQSDYI, corresponding exactly to that predicted by $G_{i\alpha-2}$ cDNAs cloned from human, rat, and mouse libraries. This sequence is compared to the homologous sequence of other G-protein alpha subunits, including bovine and human $G_{i\alpha-1}$, in Table 5. It should be noted that $G_{i\alpha-1}$ differs in sequence from the synthetic peptide at 3 residues and that rod and cone transducin-alpha and $G_{o\alpha}$ show further differences.

TABLE 5

Comparison of the amino acid sequence of the synthetic peptide corresponding to the $G_i$ subunit to homologous sequences of other G-protein alph subunits The single letter amino acid code is used.

| Transducin cone (159-168): | L D R I T A P D Y L |
|---|---|
| Transducin rod (155-164): | L E R L V T P G Y V |
| $G_{i\alpha\text{-}2}$ (160-169): | L E R I A Q S D Y I |
| $G_{i\alpha\text{-}1}$ (159-168): | L D R I A Q P N Y I |
| $G_{oi}$ | L D R I G A A D Y Q |

Figure 3A:
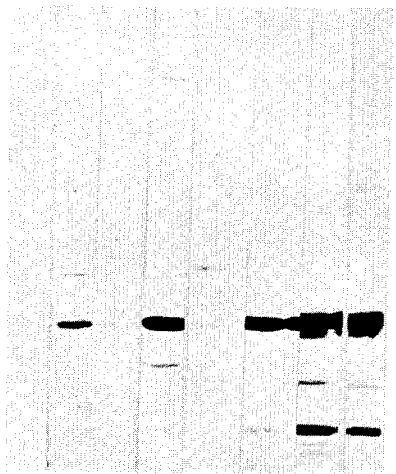
Figure 3B:
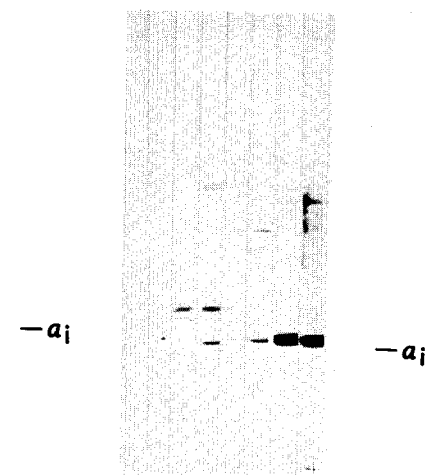

FIG. 3 shows the result s of immunoblots of human neutrophil membranes (panel A) and of bovine brain membrane cholate extract (panel B) performed with antisera against KENLKDCGLF, AS/6 and AS/7, and with antisera LE/1, 2, and 3, raised against a conjugate of the synthetic pepide LERLAQSDYI and carrier protein, KKLH. As reported earlier (Falloon et al, FEBS Letters 209:352-356,1986), AS/6 and AS/7 detect the abundant 40-41-kDa pertussis toxin substrate(s) in neutrophil membranes and in brain. The three preimmune LE sera showed no specific reactivity in either neutrophil membranes or brain cholate extract. All three LE immune sera recognized a band of similar mobility to that revealed by AS/6 and AS/7 in neutrophil membranes, with LE/1 showing weaker reactivity at equivalent dilution. In brain cholate extract, LE/1 immune antisera failed to detect specific immunoreactivity, whereas LE/2 and LE/3 revealed bands of similar mobility, but much weaker reactivity, as those seen with AS/6 and AS/7.

These results indicate that LE antisera detect a protein identical to or closely realted to $G_{i\alpha-2}$ that is particularly abundant in neutrophils and a similar or identical protein in brain that is relatively lower in abundance (compare the ratio of AS/LKE immunoreactivity in neutrophil and brain).

Figure 4A:
Figure 4B:
Figure 4B:
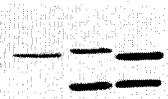
Figure 4B:
Figure 4B:

Next the reactivity of LE/3 and AS/6 was compared with purified G-protein preparations, including the major pertussis toxin substrate purified from bovine neutrophils. FIG. 4A shows the pattern of protein staining of the purified preparations from bovine neutrophil (lane 1, alpha subunit only), bovine brain (lane 2), and bovine rod outer segments (lane 3). Panel B shows the results of immunoblots of these proteins with three distinct antisera, AS/6, LE/3, and CW/6, a unique antiserum raised against holotransducin and shown to cross-react with $G_{i\alpha}$ but not Goo in brain. CW/6 as expected detects the common beta subunit in the two holoprotein preparations, reacts strongly with transducin-alpha, and with a more slowly migrating (about 41-kDa) Gio from brain. CW/6 also cross-reacts with the purified bovine neutrophil protein, but this reactivity is lower than with the brain protein (note that 1.0 µg of bovine neutrophil protein was loaded on immunoblot lanes compared with 0.5 µg on the lane stained with Coomassie Blue shown in panel A). AS/6 reacts equally well with transducin-alpha brain $G_{i\alpha}$ and neutrophil "$G_{i\alpha}$" as expected, given its ability to recognize the KENLKDCGLF and KNNLKDCGLF sequence. Note the subtle but definite differences in migration of the immunoreactive bands detected with A/6. In contrast, as expected (Table 5), LE/3 fails to react with either transducin-alpha or $G_{o\alpha}$. Consistent with the result s seen in neutrophil membranes, LE/3 strongly reacts with the purified neutrophil major pertussis toxin substrate. Interestingly, LE/3 reveals a faintly reactive band (lane 2) in the purified brain $G_I/G_o$ lane that comigrates with the purified neutrophil protein. It is highly likely that this represents reactivity of LE/3 with a protein similar, if not identical, to that in neutrophils, rather than weak cross-reactivity with the 41-kDa form of $G_{i\alpha}$ abundant in brain that is readily detected by AS/6. This is based on the clear differences in mobility of the bands detected in immunblot (FIG. 4).

The specificity of LE/2 and LE/3 was further assessed by peptides corresponding to the sequences of rod and cone transducin-alpha subunits from the region homologous to LERIAQSDYI which failed to block LE/2 or LE/3 reactivity with the neutrophil membrane protein. Comparable amounts (1 and 9 µg) of the LERIAQSDYI synthetic peptide efectively blocked LE antisera reactivity (not shown). Also, antisera raised to the synthetic peptides corresponding to rod and cone transducin-alpha sequences failed to react with the 40-41-kDa protein in neutrophil membranes, although these antisera readily react with rod and cone transducin-alpha.

Tests identical to those illustrated for antisera AS6, AS7, LE/2 and LE/3 have been performed with the other antisera listed in Table 1. These tests likewise demonstrate the specificity and utility of antisera LD/1, LD/2, GO/1 and GO/3 in discriminating between various G proteins.

From the results presented above, it is quite clear that the antisera of the present invention provide means for identification and differentiation of various G-proteins.

An antibody reagent kit comprising separate containers each containing different antibodies and optionally different antigens of the present invention, makes it possible for the first time either to quantitative or detect the presence of a specific G-protein in a biological sample. This is accomplished by standard immunological techniques employing antibodies or conjugates thereof, well known to one of ordinary skill in the art. Examples of such techniques are immunoprecipitation, enzyme linked immunosorbent assay, immunofluorescence, immunoblotting, radioimmuno assay and the like. Of course, the antisera or the antibody reagents can be cryopreserved or lyophilized for prolonged activity.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. Substantially pure, synthetic peptide having amino acid sequence selected from the group consisting of KENLKDCGLF, LERIAQSDYI, LDRIAQPNYI, ANNLRGCGLY and GCTLSAEERAALERSK.
2. The peptide of claim 1 being KENLKDCGLF.
3. The peptide of claim 1 being LERIAQSDYI.
4. The peptide of claim 1 being LDRIAQPNYI.
5. The peptide of claim 1 being ANNLRGCGLY.
6. The peptide of claim 1 being GCTLSAEERAALERSK.

* * * * *